US007807360B2

(12) United States Patent
Kim et al.

(10) Patent No.: US 7,807,360 B2
(45) Date of Patent: Oct. 5, 2010

(54) METHOD AND APPARATUS FOR CONCENTRATING AND AMPLIFYING NUCLEIC ACID IN SINGLE MICRO CHAMBER

(75) Inventors: Young-rok Kim, Yongin-si (KR); Jun-hong Min, Yongin-si (KR); In-ho Lee, Yongin-si (KR); Young-sun Lee, Yongin-si (KR); Chang-eun Yoo, Yongin-si (KR); Ki-woong Han, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 98 days.

(21) Appl. No.: 11/620,961

(22) Filed: Jan. 8, 2007

(65) Prior Publication Data
US 2007/0269819 A1 Nov. 22, 2007

(30) Foreign Application Priority Data
May 22, 2006 (KR) .................... 10-2006-0045812

(51) Int. Cl.
*C12Q 1/68* (2006.01)
(52) U.S. Cl. ........................................ 435/6
(58) Field of Classification Search ................. None
See application file for complete search history.

(56) References Cited

U.S. PATENT DOCUMENTS

| 5,234,809 | A |   | 8/1993  | Boom et al.     |         |
|-----------|---|---|---------|-----------------|---------|
| 5,824,517 | A | * | 10/1998 | Cleuziat et al. | 435/91.2 |
| 6,143,496 | A | * | 11/2000 | Brown et al.    | 435/6   |
| 6,291,166 | B1 |  | 9/2001  | Gerdes et al.   |         |
| 6,383,783 | B1 |  | 5/2002  | Haddad          |         |
| 6,440,725 | B1 | * | 8/2002  | Pourahmadi et al. | 435/288.5 |
| 6,489,112 | B1 | * | 12/2002 | Hadd et al.     | 435/6   |
| 6,743,581 | B1 | * | 6/2004  | Vo-Dinh         | 435/6   |
| 2001/0041332 | A1 | * | 11/2001 | Hillebrand et al. | 435/6 |
| 2005/0142570 | A1 |  | 6/2005  | Parthasarathy et al. |  |

FOREIGN PATENT DOCUMENTS

| WO | 02/100542 A1  | 12/2002 |
| WO | 2004061085    | 7/2004  |
| WO | 2004/103890 A1 | 12/2004 |

OTHER PUBLICATIONS

Giordano et al. ("Towards dynamic coating of glass microchip chambers for amplifying DNA via the polymerase chain reaction" Electrophoresis. Jan. 2001;22(2):334-40).*
Hourfar et al. ("High-throughput purification of viral RNA based on novel aqueous chemistry for nucleic acid isolation" Clin Chem. Jul. 2005;51(7):1217-22).*
European Search Report dated Aug. 28, 2007 for Application No. 07100033.5.
"Microfluidic handling of PCR solution and DNA amplification on a reaction chamber array biochip"; Authors: Gong, et al.; Biomed Microdevices, vol. 8, pp. 167-176 (2006).
"Microchamber array based DNA quantification and specific sequences detection from a single copy via PCR in nanoliter volumes"; Authors: Matsubara et al.; Biosensors and Bioelectronics, vol. 20, pp. 1482-1490, 2005.
"Biochemical analysis with microfluidic systems"; Authors: Bilitewski et al.; Anal Bioanal Chem, vol. 377, pp. 556-569 (2003).
"Microfluidic devices fabricated in poly9dimethylsiloxane) for biological studies"; Authors: Sia and Whitesides; Electrophoresis, vol. 24, pp. 3563-3576 (2003).
"Chip PCR. I. Surface passivation of microfabricated silicon-glass chips for PCR"; Authors: Shoffner, et al.; Nucleic Acid Research, vol. 24, No. 2, pp. 375-379 (1996).
"Integrated polymerase chain reaction chips utilizing digital microfluidics"; Authors: Chang, et al.; Biomeds Microdevices, vol. 8, pp. 215-225 (2006).
Office Action issued by the EPO on Sep. 2, 2009.
Office Action issued Feb. 12, 2010 by the Chine Patent Office.
Hourfar, et al.; "High-Throughput Purification of Viral RNA Based on Novel Aqueos Chemistry for Nucleic Acid Isolation"; Clinical Chemistry; vol. 51, No. 7; pp. 1217-1222; 2005.
Paegel, et al.; "Microfluidic devices for DNA sequencing: sample preparation and electrophoretic analysis"; Current Opinion in Biotechnology; vol. 14; pp. 42-50; 2003.
Kim, et al.; "Fabrication and characterization of a PDMS-glass hybrid continuous-flow PCR chip"; Biochemical Engineering Journal; vol. 29; pp. 91-97; 2006.
Hodko, et al.; "Detection of Pathogens Using On-Chip Electrochemical Analysis of PCR Amplified DNA Molecules"; Proceedings of SPIE; vol. 4265; pp. 65-74; 2001.

(Continued)

*Primary Examiner*—Christopher M. Babic
(74) *Attorney, Agent, or Firm*—Cantor Colburn LLP

(57) ABSTRACT

A method of sequentially performing concentration and amplification of nucleic acid in a single micro chamber includes: introducing a nucleic acid-containing sample and a solution including a kosmotropic salt to a micro chamber having a hydrophilic interior surface to concentrate the nucleic acid by binding the nucleic acid on the interior surface of the micro chamber; and performing a polymerase chain reaction (PCR) by adding a PCR mixture to the chamber. Since the nucleic acid is reversibly bound to the interior surface of the micro chamber, PCR yield is higher compared with a surface of aluminum oxide in which irreversible binding occurs. In addition, all processes are sequentially performed in a single micro chamber so that the number of samples, consumables, time, and labor for treatment and analysis can be reduced, detection sensitivity can be improved, and risk of sample cross contamination significantly reduced without sample loss by eliminating transporting of the sample. A complete automated system for concentration and amplification of nucleic acid is thus readily provided.

12 Claims, 8 Drawing Sheets

OTHER PUBLICATIONS

Cheng, et al.; Chip PCR. II. Investigation of different PCR amplification systems in microfabricated silicon-glass chips; Nucleic Acids Research; vol. 24, No. 2; pp. 380-385; 1996.

Zhang, et al.; "PCR microfluidic devices for DNA amplification"; Biotechnology Advances; vol. 24; pp. 243-284; 2006.

Samper, et al.; "Microfluidic Sample Preparation for Nucleic Acid Analysis"; IEEE Proceedings 2004 International SINAIA Romania Oct. 4-6, 2004; pp. 51-58; Oct. 4, 2004.

Park, et al.; Cylindrical Pillars in Silicon PCR Chip Enhance the Performance of DNA Amplification; The 13th International Conference on Solid-State Sensors, Actuators and Microsystems; pp. 1604-1607; Jun. 5-9, 2005.

Panaro, et al.; "Micropillar array chip for intergrated white blood cell isolation and PCR"; Biomolecular Engineering; vol. 21; pp. 157-162; 2005.

Liu, et al.; "Environmental microbiology-on-a-chip and its future impacts"; Trends in Biotechnology; vol. 23, No. 4; pp. 174-179; Apr. 2005.

Preliminary Examination for European Application No. 07100033.5.

* cited by examiner

CHIP #1

CHIP #2

CHIP #3

CHIP #4

CHIP #5

CHIP #6

METHOD AND APPARATUS FOR CONCENTRATING AND AMPLIFYING NUCLEIC ACID IN SINGLE MICRO CHAMBER

This application claims priority to Korean Patent Application No. 10-2006-0045812, filed on May 22, 2006, and all the benefits accruing therefrom under 35 USC §119(a) the disclosure of which is incorporated herein by reference in its entirety.

BACKGROUND OF THE INVENTION

1. Field of the Invention

The present invention relates to a method and apparatus for concentrating and amplifying nucleic acid in a single micro chamber.

2. Description of the Related Art

The production of high purity double-stranded plasmid DNAs, single-stranded phage DNAs, chromosomal DNAs, and agarose gel-purified DNA fragments is very important in molecular biology. Ideal methods of purifying DNAs should be simple and quick, and include little additional manipulation of samples. DNAs obtained using such methods can be used for direct transformation, restriction enzyme analysis, ligation, or sequencing. Such methods are very attractive in the automated production of DNA samples, which is favored in research and diagnosis labs.

Conventionally, a method of purifying nucleic acid using a solid phase is known. For example, U.S. Pat. No. 5,234,809 discloses a method of purifying nucleic acid using a solid phase to which nucleic acids are bound, the method including: mixing a starting material, a chaotropic (i.e., water-disrupting) material, and a nucleic acid binding solid phase; separating the solid phase with the nucleic acid bound thereto from the liquid, and washing the solid phase nucleic acid complexes. However, this method is time consuming and complicated, and thus is not suitable for a Lab-On-a-Chip ("LOC") devices and applications. The method also has a problem in that a chaotropic material must be used.

U.S. Pat. No. 6,291,166 discloses a method of archiving nucleic acid using a solid-phase matrix. This method is advantageous in that since nucleic acids are irreversibly bound to a solid-phase matrix, delayed analysis or repeated analysis of the nucleic acid solid-phase matrix complex after storage is possible. However, according to this method, alumina, which has a positively charged surface, is rendered hydrophilic by addition of basic materials, such as NaOH. Nucleic acids are irreversibly bound to the hydrophilic alumina, and thus cannot be separated from the alumina. Accordingly, the method suffers in that Polymerase Chain Reaction ("PCR") yield is low in the solid-phase matrix to which DNA is are irreversibly bound.

U.S. Pat. No. 6,383,783 discloses a method of isolating nucleic acid from a sample, the method including: introducing a sample containing target nucleic acids on a hydrophobic organic polymer solid-phase in order to attach a target nucleic acid to a solid-phase; and adding a non-ionic surfactant to the solid-phase and removing the attached target nucleic acid. However, while nucleic acids are separated using a hydrophobic solid-phase in the conventional method, it is desirable to perform additional steps in the presence of the separated nucleic acid.

BRIEF SUMMARY OF THE INVENTION

The deficiencies of the prior art are overcome by the present invention which, in an embodiment, provides a method of sequentially performing nucleic acid concentration and amplification in a single chamber which can minimize sample loss, time and cost.

In another embodiment, an apparatus for sequentially performing concentration and amplification of nucleic acid comprises: a micro chamber having a hydrophilic functional group disposed on an interior surface of the micro chamber; a kosmotropic salt solution storing part; a polymerase chain reaction (PCR) mixture storing part; and a heating part and cooling part.

In another embodiment, an apparatus for sequentially performing concentration and amplification of nucleic acid comprises: a chip including a micro chamber having a hydrophilic functional group disposed on an interior surface of the micro chamber; and a nucleic acid amplification part comprising the chip mounted thereon.

In another embodiment a lab-on-a-chip includes the apparatus for concentrating and amplifying nucleic acid.

BRIEF DESCRIPTION OF THE DRAWINGS

The above and other features and advantages will become more apparent by describing in detail exemplary embodiments thereof with reference to the attached drawings in which.

DETAILED DESCRIPTION OF THE INVENTION

Figure 1:
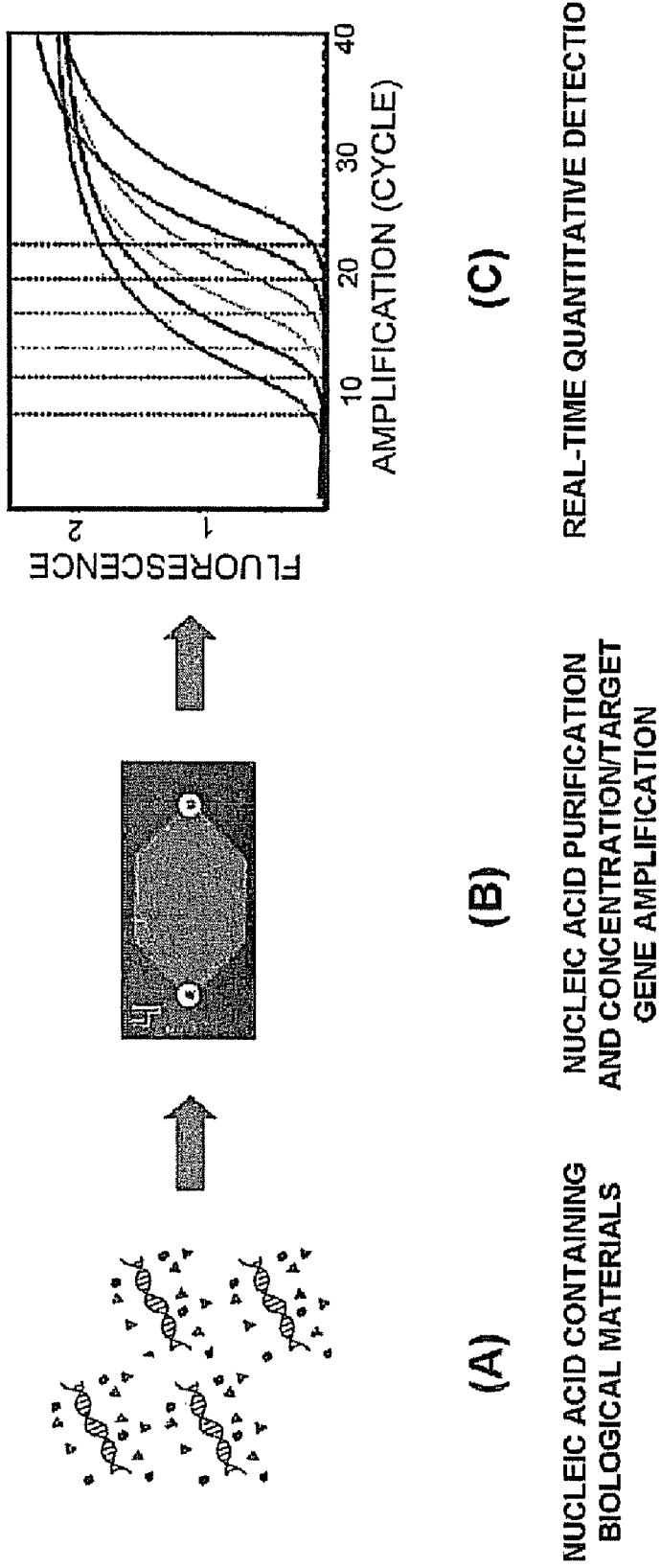
FIG. 1 is a view illustrating an exemplary process by which concentration and amplification of nucleic acid are performed in a single micro chamber, according to an embodiment.

The present invention will now be described more fully with reference to the accompanying drawings, in which exemplary embodiments of the invention are shown.

It will be understood that when an element is referred to as being "on" another element, it can be directly on the other element or intervening elements may be present therebetween. In contrast, when an element is referred to as being "disposed on" another element, the elements are understood to be in at least partial contact with each other, unless otherwise specified.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Surprisingly, a method of concentrating and amplifying nucleic acid is effectively sequentially performed in a single micro chamber such that by adding a kosmotropic (i.e., water-structuring) salt to a micro chamber having a hydrophilic functional group disposed on its interior surface, nucleic acids are concentrated in the micro chamber, and PCR is performed in the micro chamber using the concentrated nucleic acid.

According to an embodiment, there is provided a method of sequentially performing concentration and amplification of nucleic acid in a single chamber, the method comprising: introducing a nucleic acid-containing sample and a solution comprising a kosmotropic salt to a micro chamber having a hydrophilic interior surface to concentrate nucleic acid by binding the nucleic acid on the interior surface of the micro chamber; and performing PCR by adding a PCR mixture to the chamber.

The present invention relates to a method for preparing a sample for nucleic acid analysis and performing real-time PCR in a single micro chamber. To amplify and detect target genes, DNA has to be isolated and purified from a biological sample. Various impurities that are present in cell lysate and inhibit PCR are removed by a purification step. In a conventional process, purification, amplification and detection of specific genes are performed in a separate micro chamber which consumes excessive time and costs during gene analysis, and also significantly increases the possibility of cross contamination of the samples being tested. In the present invention, nucleic acid purification and concentration and nucleic acid amplification are integrated, and thus both the analysis processes are simplified and the risk of cross contamination is reduced.

FIG. 1 is a view illustrating how concentration and amplification of nucleic acid are performed in a single micro chamber, according to an embodiment of the method. A target gene is purified and concentrated from a biological sample (A) including nucleic acid in a single micro chamber (B), and then the purified and concentrated target gene is amplified in the micro chamber (B) to be detected in real time (C). However, several requirements have to be satisfied for this. First, reagents used in DNA purification and concentration should not affect the real-time polymerase chain reaction (PCR), and therefore PCR inhibitors such as a chaotropic salts and ethanol cannot be used. Second, PCR has to be performed on a $SiO_2$ chip having a large surface area, but the increased surface of $SiO_2$ acts as a PCR inhibitor, so that an additive needs to be added to reduce PCR inhibition. Third, the $SiO_2$ chip has to have a high DNA binding efficiency.

To solve these problems, a kosmotropic salt is used instead of the chaotropic salt that is conventionally used in the purification of nucleic acids. When a chaotropic salt is used, the surface of a micro chamber is dehydrated and nucleic acid can be directly bound to the micro chamber by hydrogen bonding, so that binding of nucleic acid is affected by pH and a chaotropic salt acts as a PCR inhibitor. However, when a kosmotropic salt is used, the surface of the micro chamber exposed to the kosmotropic salt is hydrated so that a stabilized water layer is formed on the surface of the micro chamber so exposed. Nucleic acid can be adsorbed onto the surface of the micro chamber by hydrogen bonding to the water layer, resulting from a salting-out effect by hydrophilic interaction.

Figure 2:
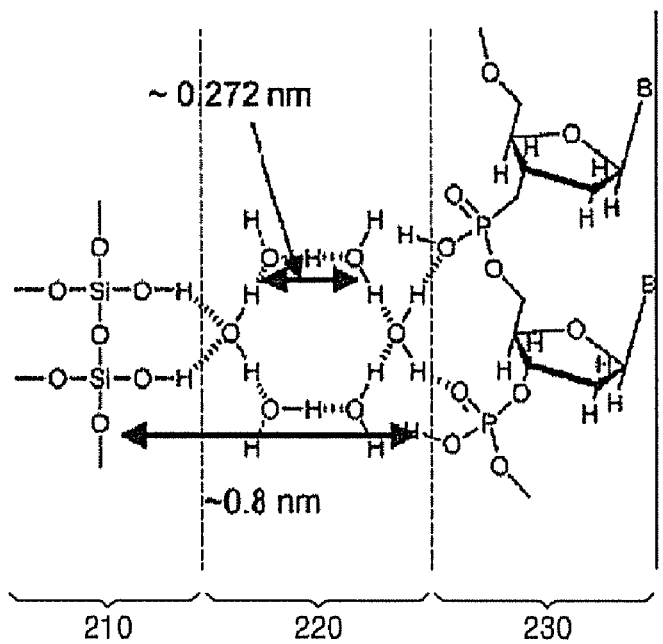
FIG. 2 is a view illustrating an exemplary process by which nucleic acid is bound on a hydrophilic surface of a micro chamber in the presence of a kosmotropic salt, according to an embodiment.

FIG. 2 is a view illustrating how nucleic acid is bound on a hydrophilic surface of a micro chamber in the presence of a kosmotropic salt, according to an embodiment. As can be seen in FIG. 2, due to the salting-out effect of the kosmotropic salt, a silica substrate 210 (left part of FIG. 2) is bound with water by hydrogen bonding, and the formed water layer 220 (middle part of FIG. 2) forms a hydrogen bond with nucleic acid 230 (right part of FIG. 2) again so that the nucleic acid is bound to the micro chamber by means of the stabilized water layer. Therefore, nucleic acid binding with a micro chamber does not require acidic conditions that are conventionally used for binding nucleic acids, and the interior surface of the micro chamber need not be limited to silica.

In the method of amplifying nucleic acid according to an embodiment, when a sample containing nucleic acid and a solution containing a kosmotropic salt are introduced into the interior of the micro chamber, water forms a hydrogen bond on an interior surface of the micro chamber due to the salting-out effect of the kosmotropic salt to provide a water layer, and the water layer so formed then forms a hydrogen bond with the nucleic acid, and as a result, the nucleic acid is bound to the interior surface of the micro chamber. By washing out other components of the nucleic acid-containing sample except for nucleic acid not bound to the interior surface of the micro chamber after the binding of the nucleic acid to the interior surface of the micro chamber, the bound nucleic acid can then be concentrated in a purer form (i.e., purified). A washing solution can thus be passed through the micro chamber over the interior surface of the micro chamber having the nucleic acid bound to it to remove any of the nucleic acid-containing sample that is not bound. The washing solution has a concentration of kosmotropic salt that is lower than that of the kosmotropic salt solution used when the nucleic acid is being bound to the interior surface of the micro chamber.

In the method of amplifying nucleic acid according to the current embodiment, a PCR mixture is added to a micro chamber in which nucleic acid is concentrated, and then PCR is performed using a target nucleic acid that is bound to an interior surface of the micro chamber, or isolated from the interior surface of the micro chamber. It will be understood by those skilled in the art that the composition and concentration of the PCR mixture vary depending on the polymerase introduced. In addition, PCR conditions can be appropriately selected according to a length of a PCR product to be amplified, sequence homology between a template and a primer, a length of a primer and the like.

In the method of concentrating and amplifying nucleic acid according to the current embodiment, polyethylene glycol and bovine serum albumin ("BSA") can be added in the PCR process. the $SiO_2$ interior surface of the micro chamber acts as a PCR inhibitor where the micro chamber interior surface has a large surface area, and thus an additive is added to reduce PCR inhibition. Thus, in an embodiment, PCR amplification efficiency is increased by adding polyethylene glycol ("PEG") and bovine serum albumin (BSA). The concentration of the polyethylene glycol and bovine serum albumin (BSA) can be 1-10% by volume and 0.1-10 mg/ml, respectively. When the concentration of PEG and BSA is beyond these ranges, PCR amplification efficiency decreases.

In the method of concentrating and amplifying nucleic acid according to the current embodiment, the interior surface of the micro chamber can have a plurality of pillars. In an embodiment, to increase the opportunity of contacting a sample containing nucleic acid with the micro chamber, the interior surface of the micro chamber has a pillar structure having a large surface area rather than a planar structure. The pillars can have various shapes, such as a square, rectangle, diamond, cylinder, cone, hexagon, octagon and the like. The interval between the pillars may be 8 to 50 μm. When the interval between the pillars is beyond this range, binding and amplification efficiency of the nucleic acid decreases.

In the method of concentrating and amplifying nucleic acid according to the current embodiment, the micro chamber has a hydrophilic functional group on an interior surface of the micro chamber, where the hydrophilic functional group can be any hydrophilic group such as a hydroxyl group, an amine group, a carboxyl group, a polycarboxyl group, a silanol group, or the like.

In the method of concentrating and amplifying nucleic acid according to the current embodiment, the kosmotropic salt can be sulfate ($SO_4^{2-}$), phosphate ($HPO_4^{2-}$), hydroxide ($OH^-$), fluoride ($F^-$), formate ($HCOO^-$), acetate ($CH_3COO^-$), or like salts, but is not limited thereto. The kosmotropic salt induces protein crystallization, acts as a salting-out ion for a hydrophobic particle, and forms a water structure according to the Hofmeister series.

In the method of concentrating and amplifying nucleic acid according to the current embodiment, the sample containing nucleic acid and a solution comprising a kosmotropic salt may have a pH of 3-10. When the pH of the solution including the sample containing nucleic acid and the solution comprising a kosmotropic salt is beyond this range, DNA can be physically and chemically denatured and subsequent processing can be adversely affected.

In the method of concentrating and amplifying nucleic acid according to the current embodiment, the concentration of the kosmotropic salt can be 100 to 2,000 millimolar ("mM"). When the concentration of the kosmotropic salt is less than 100 mM, binding efficiency of the nucleic acid that is bound to the micro chamber is decreased. When the concentration of the kosmotropic salt is greater than 2,000 mM, it is difficult to prepare a useful solution due to limited buffer solubility and excessive buffer concentration.

In the method of concentrating and amplifying nucleic acid according to the current embodiment, the sample containing the nucleic acid can be blood, serum, urine, saliva or cell lysate of bacteria existing in a cell culture fluid, but is not limited thereto. The sample containing the nucleic acid according to an embodiment may be from a mammal, a plant, bacteria, or yeast. The sample can be in a single cell form or tissue form, and the cell or tissue may stem from cultures in vitro.

According to another embodiment, there is provided an apparatus for sequentially performing concentration and amplification of nucleic acid, the apparatus comprising: a micro chamber having a hydrophilic functional group on its interior surface; a nucleic acid-containing sample storing part that is interconnected to the micro chamber through a first microchannel and provides the micro chamber with the nucleic acid-containing sample; a kosmotropic salt solution storing part that is interconnected to the micro chamber through a second microchannel, and provides the micro chamber with a kosmotropic salt; a PCR mixture storing part that is interconnected to the micro chamber through a third microchannel, and provides the micro chamber with a PCR mixture; and a heating part and cooling part that heat and cool the micro chamber.

The apparatus for concentrating and amplifying nucleic acid according to the current embodiment comprises a micro chamber having a hydrophilic functional group on its interior surface, a nucleic acid-containing sample storing part, a kosmotropic salt solution storing part, a PCR mixture storing part, and a heating part and cooling part. In the apparatus for concentrating and amplifying nucleic acid according to the current embodiment, the micro chamber comprises a chamber within a chip, and has a hydrophilic functional group on its interior surface so that it forms a hydrogen bond with water to form a water layer that is stable. The formed stable water layer binds with nucleic acid. The hydrophilic functional group can be any hydrophilic group such as, for example, a hydroxyl group, an amine group, a carboxyl group, a polycarboxyl group, a silanol group, or the like.

The nucleic acid-containing sample storing part is a part that provides the micro chamber with the nucleic acid-containing sample, and is interconnected to the micro chamber through a first microchannel.

The kosmotropic salt solution storing part is a part that provides the micro chamber with the kosmotropic salt, and is also interconnected to the micro chamber through a second microchannel. When a sample containing nucleic acid to be isolated is introduced to the apparatus (through the first microchannel), the kosmotropic salt solution storing part provides the micro chamber with the kosmotropic salt (through the second microchannel), the nucleic acid-containing sample and the kosmotropic salt are mixed in the apparatus, and the nucleic acid is bound to the micro chamber due to a salting-out effect of the kosmotropic salt.

The PCR mixture storing part is a part that provides the micro chamber with the PCR mixture, and is interconnected to the micro chamber through a third microchannel. After the nucleic acid is concentrated in the micro chamber, the PCR mixture storing part injects the PCR mixture (through the third microchannel) into the micro chamber to perform PCR.

The heating part and cooling part are parts that heat and cool the micro chamber, and when the PCR mixture is introduced in the micro chamber, the heating part and cooling part control a temperature of the micro chamber by heating and cooling according to PCR conditions.

In the apparatus for concentrating and amplifying nucleic acid according to the current embodiment, the interior surface of the micro chamber may have a plurality of pillars. To increase the amount of contact between the sample containing nucleic acid and the interior surface of the micro chamber, in an embodiment, the interior surface of the micro chamber can have a pillar structure having a large surface area rather than a planar structure. The pillars can have various shapes, such as a square, rectangle, diamond, cylinder, cone, hexagon, octagon or the like. The interval between the pillars may be 8 to 50 μm. When the interval between the pillars is beyond this range, binding and amplification efficiency for the nucleic acid decreases.

In the apparatus for concentrating and amplifying nucleic acid according to the current embodiment, the sample containing the nucleic acid can be blood, serum, urine, saliva or cell lysate of bacteria existing in a cell culture fluid, but is not limited thereto. The sample containing the nucleic acid according to an embodiment may be from a mammal, a plant, bacteria, or yeast. The sample can be in a single cell form or tissue form, and the cell or tissue may stem from cultures in vitro.

According to another embodiment, there is provided an apparatus for sequentially performing concentration and amplification of nucleic acid, the apparatus comprising: a chip including a micro chamber having a hydrophilic functional group on its interior surface; and a nucleic acid amplification part comprising the chip mounted thereon (i.e., on which the chip is mounted). The apparatus for concentrating and amplifying nucleic acid according to the current embodiment comprises a chip and a nucleic acid amplification part, and the chip includes a micro chamber having a hydrophilic functional group on its interior surface, where the chip comprises a single chamber. The micro chamber has a hydrophilic functional group on its interior surface so that when a nucleic acid-containing sample and a solution comprising kosmotropic salt are introduced to the micro chamber, the nucleic acid is bound on an interior surface of the micro chamber and the nucleic acid is concentrated. The nucleic acid amplification part includes the chip thereon, and amplifies nucleic acid concentrated in the micro chamber of the chip. The chip including the micro chamber in which the nucleic acid is concentrated is placed in the nucleic acid amplification part, and a PCR mixture is introduced in the micro chamber and PCR is then performed to amplify the concentrated nucleic acid.

According to another embodiment, there is provided a lab-on-a-chip including the apparatus for concentrating and amplifying nucleic acids. In the apparatus for concentrating and amplifying nucleic acid according to an embodiment, each functional element can be implemented by process-on-a-chip using a known microfluidics technique and a MEMS device, and can be further implemented by a lab-on-a-chip.

Hereinafter, the present invention will be described in further detail with reference to the following examples. These examples are for illustrative purposes only and are not intended to limit the scope.

EXAMPLE 1

PCR Efficiency as a Function of Increasing Surface Area of a Chip

PCR efficiency was determined as a function of increasing surface area of a chip. PCR was performed using a TMC1000 (Samsung) instrument. The TMC1000 is an instrument that performs quantitative PCR on a silicon-based chip. Unless otherwise specified, a template DNA used in all the examples is a genome DNA of E. coli BL21, $1.4 \times 10^5$ copies of which were used per reaction. A copy of genome DNA has seven target nucleic acids (16s-rRNA gene), and thus a total of $10^6$ copies of the target gene per reaction are included. A forward primer (YCCAKACTCCTACGGGAGGC; SEQ ID NO: 1) and a reverse primer (GTATTACCGCRRCTGCTGGCAC; SEQ ID NO: 2) were used as a PCR primer.

Unless otherwise specified, a PCR mixture comprises 1×PCR buffer (Solgent Co. Ltd.), 5.0 mM of $MgCl_2$, 200 μM of dNTP, 0.2 μM of each primer, 0.1 mg/ml of BSA, and 0.1 U/μl of Taq DNA polymerase. Temperature condition of PCR is as follows. PCR was performed in an Eppendorf PCR tube at 94° C. for 5 minutes for a cycle, and at 94° C. for 30 seconds, at 62° C. for 30 seconds and at 72° C. for 30 seconds for 30 cycles, and then the obtained PCR product was quantified using Bioanalyzer (Agilent). PCR in a chip was performed at 94° C. for 1 minute for a cycle, and at 94° C. for 5 seconds, at 62° C. for 5 seconds and at 72° C. for 20 seconds for 40 cycles, and then the obtained PCR product was monitored in real time using the TMC1000 (Samsung) instrument.

Figure 3:
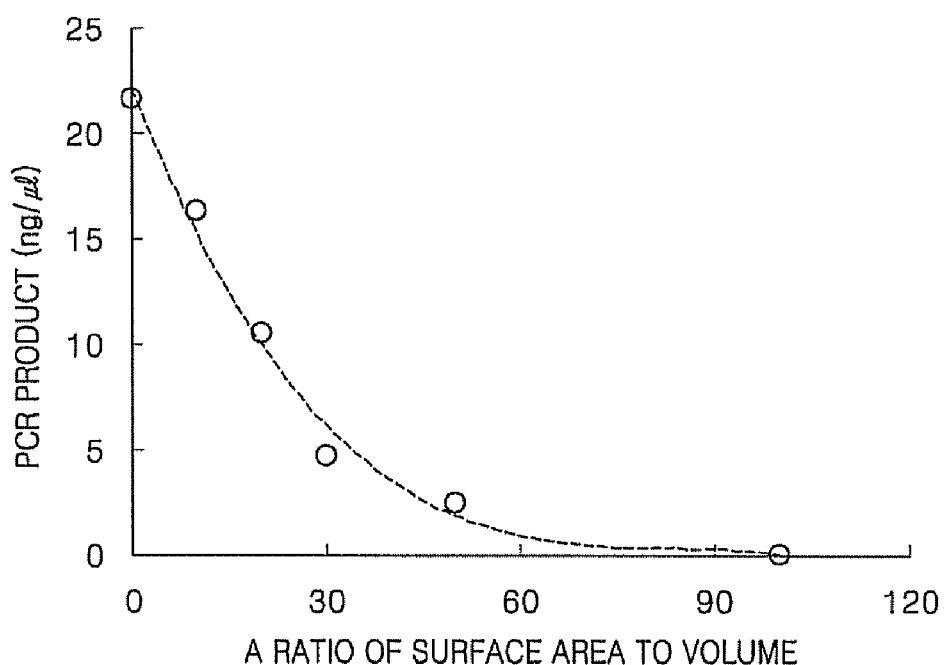
FIG. 3 is a graph showing exemplary polymerase chain reaction (PCR) efficiency corresponding to an increase in a chip surface area, according to an embodiment.

FIG. 3 is a graph showing PCR efficiency as a function of increasing chip surface area, according to an embodiment. Referring to FIG. 3, it can be seen that the higher the ratio of chip surface area to volume, the less the amount of PCR product obtained, and further the amount of the produced PCR product is closely related to the ratio of the chip surface area to volume. Therefore, to perform PCR using a chip having a large surface area, other additives for reducing PCR inhibition need to be added.

EXAMPLE 2

PCR Efficiency as a Function of PEG Concentration

Figure 4:
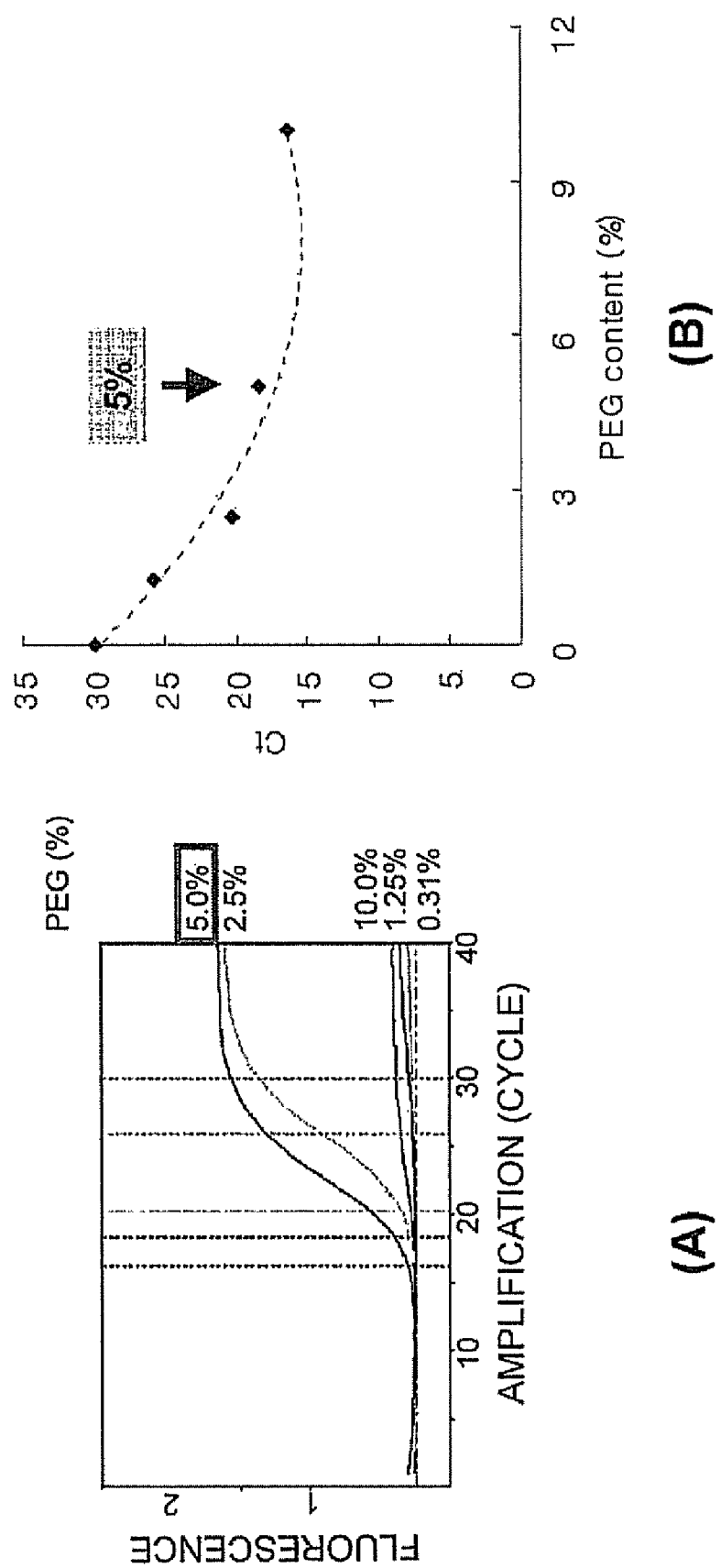
FIGS. 4A and 4B each illustrate a graph showing exemplary PCR efficiency by fluorescence (FIG.4A) and by count (FIG.4B) with respect to polyethylene glycol ("PEG") concentration, according to an embodiment.

PCR efficiency as a function of concentration of polyethylene glycol (PEG) with respect to a chip having a large surface area was determined. PCR was performed in the same manner as in Example 1 except that 5 samples were prepared by adding PEG in concentrations of 0.31 wt %, 1.25 wt %, 2.5 wt %, 5 wt %, and 10 wt % to a PCR mixture, based on the total weight of PCR mixture. FIG. 4 illustrates two graphs ((A) and (B)) showing PCR efficiency with respect to PEG concentration. In FIG. 4, the graph on the left (A) refers to Rn values, and the graph on the right (B) refers to fluorescence measurement values Ct. The fluorescence measurement values Ct are represented by determining the amount of fluorescence amplified in real time as a threshold cycle. When the same sample is used, the lower the Ct value is, the higher the PCR efficiency. Ct is a unit indicating that 1 cycle difference denotes doubling or halving DNA concentration. Rn is related to the concentration of PCR product, and the higher the Rn value is, the higher the concentration of PCR product. Thus as shown in FIG. 4, when 5% (w/w) of PEG is added based on the total weight of PCR mixture, Rn has the highest value, and Ct has the lowest value, representing the highest PCR efficiency.

EXAMPLE 3

PCR Efficiency According to a Concentration of BSA

Figure 5:
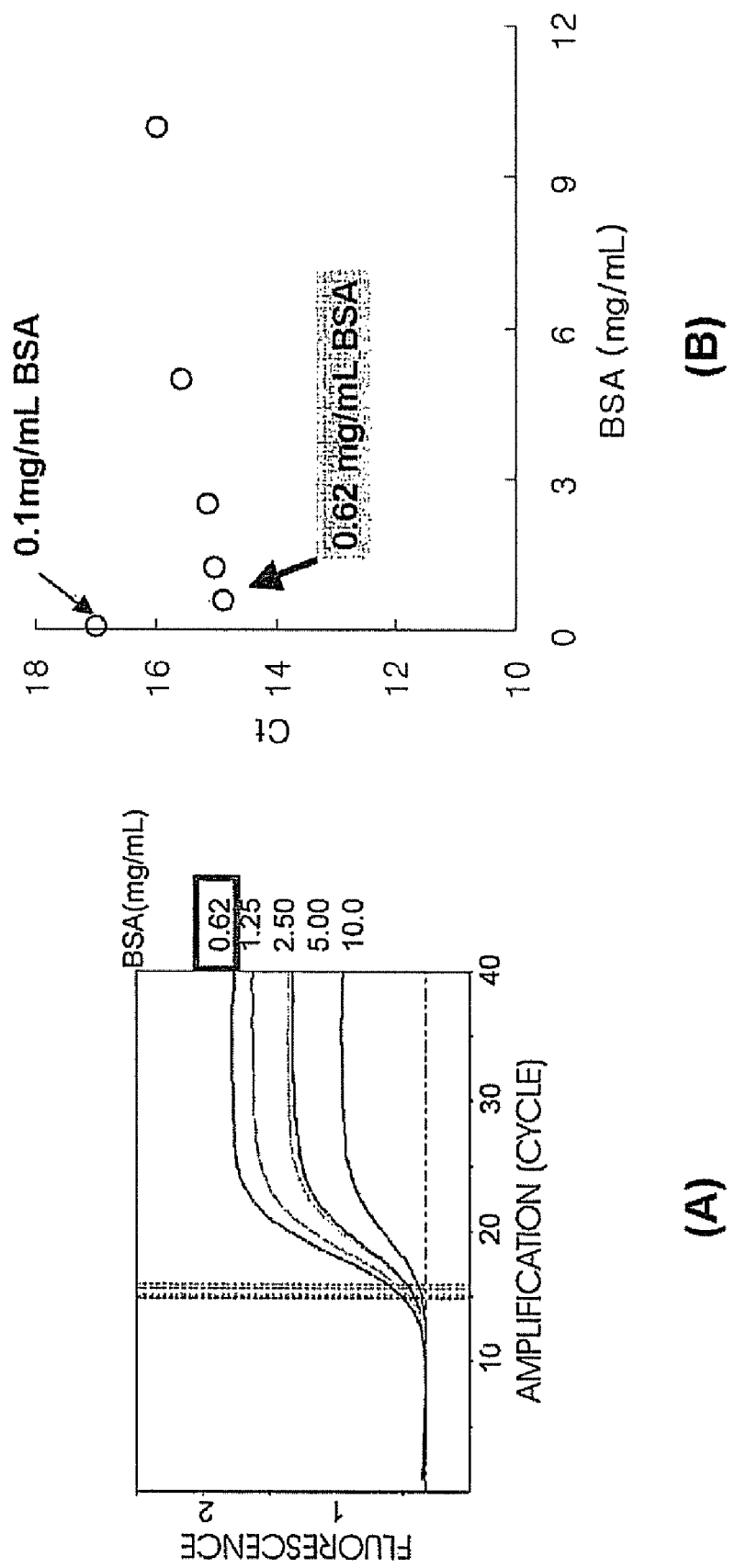
FIGS. 5A and 5B each illustrate a graph showing exemplary PCR efficiency by fluorescence (FIG.5A) and by count (FIG.5B) with respect to Bovine Serum Albumin ("BSA") concentration, according to an embodiment.

PCR efficiency as a function of the concentration of bovine serum albumin (BSA) with respect to a chip having a large surface area was determined. PCR was performed in the same manner as in Example 1, except that 5% (w/w) of PEG was added to a PCR mixture based on the total weight of PCR mixture, and 5 samples were prepared by adding amounts of 0.62 mg/ml, 1.25 mg/ml, 2.5 mg/ml, 5 mg/ml, and 10 mg/ml of BSA were added thereto, based on the total volume of PCR mixture. FIG. 5 illustrates two graphs ((A) and (B)) showing PCR efficiency as a function of BSA concentration. In FIG. 5, the graph on the left panel (A) refers to Rn values, and the graph on the right (B) refers to Ct values. Thus as shown in FIG. 5, when 0.62 mg/ml of BSA is added, Rn has the highest value, and Ct has the lowest value, representing the highest PCR efficiency.

EXAMPLE 4

PCR Efficiency According to Chips Having Various Surface Areas

To determine PCR efficiency for chips having various surface areas, 6 kinds of chips were prepared. A process of preparing a silicon-based chip ($Si/SiO_2$) and as used herein is as follows:

(1) Wafer washing

A wafer was treated in a Piranha solution ($H_2SO_4$: $H_2O_2$=3:1 v/v, 120° C.) for 15 minutes, and dried after washing under running water.

(2) Hexamethyldisilazane ("HMDS") coating 5 ml of hexamethyldisilazane (HMDS) was coated on the washed wafer using a spin coater, where coating was performed at 500 rpm for 5 seconds and at 4,000 rpm for 40 seconds, and then the coated wafer was baked in a hot plate at 120° C. for two minutes.

(3) PR coating 5 ml of photoresist (GXR601, available from AZ Electronic Materials) was coated on the baked wafer, and then coating was performed at 500 rpm for 5 seconds and at 4,000 rpm for 40 seconds.

(4) Soft baking

The PR-coated wafer was baked at 95° C. for two minutes using a hot plate.

(5) UV exposure

A mask for manufacturing a pillar was installed in a UV aligner (i-line), and the photoresist coated wafer was irradiated at a dose of 250 $mJ/cm^2$ at 365 nm UV wavelength.

(6) Development

Development was performed using a MIF 300 (AZ Electronic Materials) developer.

(7) Hard baking

The developed wafer was hard baked at 115° C. for two minutes.

(8) Deep RIE

The hard baked wafer was etched with 100 μm of Si using a STS ICP-RIE device.

(9) Ashing

Photoresist was ashed from the etched wafer using an Asher device.

(10) PR strip

The ashed wafer was treated in a Piranha solution for 15 minutes, washed and dried in order to remove and wash remaining PR.

(11) Hydrogen Fluoride (HF) process

The resulting wafer was treated with diluted HF for one minute, and natural oxide was removed.

(12) Si oxidation

For $SiO_2$ development, thermal wet oxidation was performed using vapor to develop a thickness of 3,000 A.

(13) Wafer washing

The wafer was treated in a Piranha solution for 15 minutes, washed and dried.

(14) Anodic bonding

A glass substrate was placed on the washed wafer in step (13) and 400° C. of heat and a voltage of 1,000 volts were applied thereto to complete a microchip.

Figure 6:
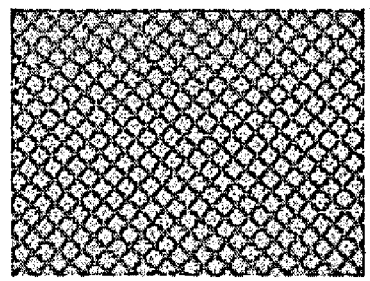
FIG. 6 illustrates photos representing six different exemplary chips having various surface areas, according to embodiments.
Figure 6:
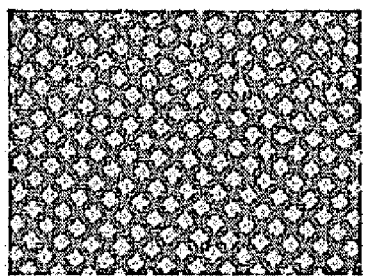
Figure 6:
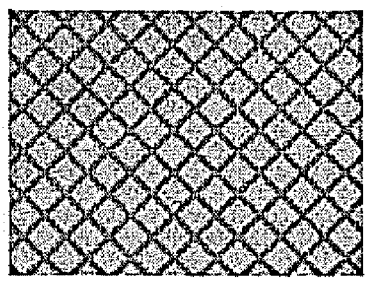
Figure 6:
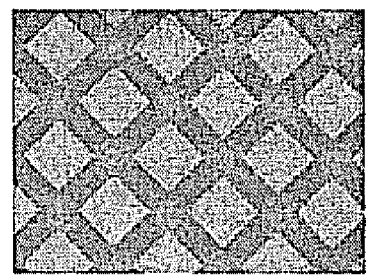
Figure 6:
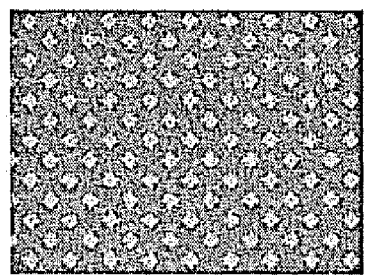
Figure 6:
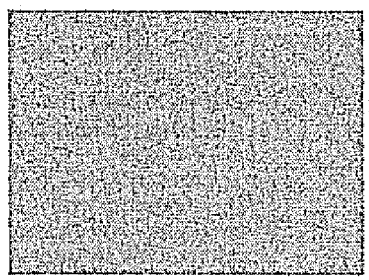

FIG. 6 illustrates photos representing six kinds of chips having various interior surface areas, according to an embodiment. Pillar size, interval between pillars, pillar height, total surface area, volume that can introduce a sample and ratio of surface area to volume are shown in Table 1.

TABLE 1

| | Chip number | | | | | |
|---|---|---|---|---|---|---|
| | 1 | 2 | 3 | 4 | 5 | 6 |
| Pillar size (μm) | 25 | 25 | 50 | 100 | 25 | 0 |
| Interval between pillars (μm) | 8 | 17 | 9 | 50 | 30 | — |
| Pillar height (μm) | 100 | 100 | 100 | 100 | 100 | 100 |
| Total surface area in $mm^2$, (and relative area vs Chip 6) | 451.6 (5x) | 313.2 (3.48x) | 283.9 (3.15x) | 130 (1.44x) | 220.2 (2.45x) | 90 (1x) |
| Chamber volume (μl) | 1.92 | 2.91 | 1.27 | 2.5 | 3.57 | 4.5 |
| Ratio of surface area to volume (rel. to Chip 6) | 11.6 | 5.33 | 11.1 | 2.95 | 3 | 1 |

DNA binding efficiency and PCR efficiency with respect to the prepared chip were determined. To measure DNA binding efficiency, the following buffer described as follows was used. An aqueous mixture of sodium sulfate and sodium acetate (1 M in each salt, pH 3.0) was used as the binding buffer, and an aqueous mixture of sodium sulfate and sodium acetate (0.01 M in each salt, pH 3.0) was used as the washing buffer. First, a sample including DNA was mixed with the binding buffer in a ratio of 1:1 v/v, the mixture was added to a chip, and subsequently the chip washed by adding the washing buffer to the chip. The amount of DNA included in the binding buffer and washing buffer from the chip was quantified using picogreen (Invitrogen/Molecular Probes), and the amount of DNA bound to the chip was predicted by the difference between the quantified DNA amount and an amount of DNA existing in an initial sample.

Figure 7:
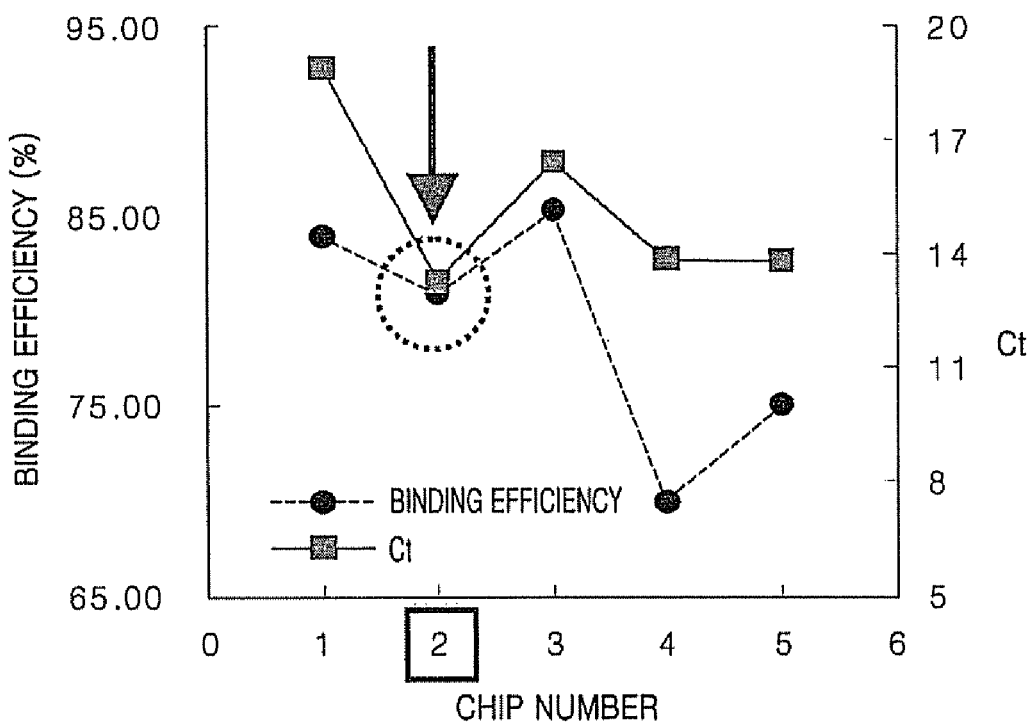
FIG. 7 is a graph showing exemplary DNA binding efficiency and PCR efficiency of 6 chips having various surface areas, according to an embodiment.

PCR was performed in the same manner as in Example 1, except that 5% (w/w) of PEG (based on the total weight of PCR mixture) and 0.62 mg/ml of BSA were added to the PCR mixtures used with each chip. FIG. 7 is a graph showing DNA binding efficiency and PCR efficiency according to 6 chips having various surface areas, according to an embodiment. As shown in FIG. 7, in the case of Chip number 2 having a pillar size of 25 μ/m and an interval between pillars of 17 μm, Ct has the lowest value, and DNA binding efficiency is high (represented by an arrow in FIG. 7). From the results, it can be seen that DNA binding efficiency is generally proportional to the surface area of a chip, and the larger the surface area is, the higher the DNA binding efficiency is. However, the larger the surface area of a chip, the higher the Ct value, and thus PCR efficiency decreases.

EXAMPLE 5

Figure 8:
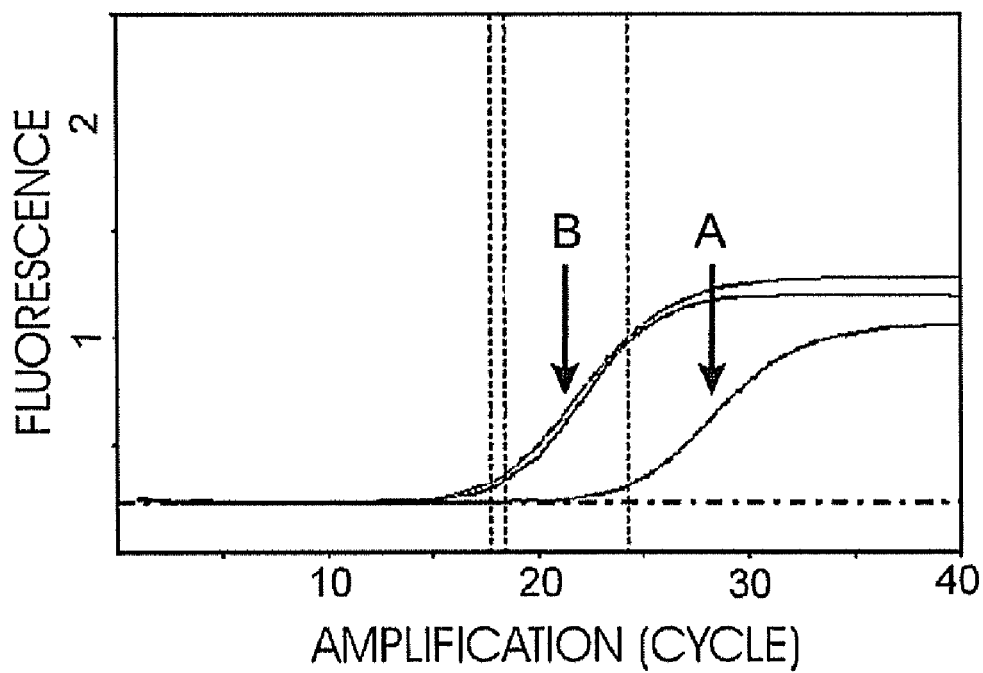
FIG. 8 is a graph showing an exemplary increase of PCR efficiency according to nucleic acid concentration, according to an embodiment.

Concentration and Amplification Efficiency of Nucleic Acid Using Purified DNA Concentration and amplification efficiency of nucleic acid was determined using purified 0.012 ng/μl of *E. coli* BL21 gDNA (16700 target gene copy/μl). In DNA concentration, an aqueous mixture of sodium sulfate and sodium acetate (1 M in each salt, pH 3.0) was used as a binding buffer, and an aqueous mixture of sodium sulfate and sodium acetate (0.01 M in each salt, pH 3.0) was used as a washing buffer. PCR was performed in the same manner as in Example 4. FIG. 8 is a plot showing PCR efficiency as a function of nucleic acid concentration. In FIG. 8, curve A represents results of performing PCR for nucleic acid from an initial DNA solution prior to concentration, and two curves B (corresponding to two replicate runs) represent PCR results of DNA concentrated using the method of concentrating and amplifying nucleic acid according to an embodiment. As shown in FIG. 8, Ct after concentration has a significantly lower value compared with Ct prior to concentration. Therefore, when the method of concentrating and amplifying nucleic acid according to an embodiment is used, DNA is efficiently bound to the interior surface of the micro chamber and thereby concentrated in the chip.

To quantitatively estimate the concentration efficiency of nucleic acid using the method of concentrating and amplifying nucleic acid according to an embodiment, Ct values based on the gDNA copy number of *E. coli* BL21 as a template were measured. The results are shown in Table 2.

TABLE 2

| DNA(target gene copy/chip) | Ct |
|---|---|
| 3.00E+06 | 14.86 |
| 1.00E+06 | 16.77 |
| 3.33E+05 | 18.22 |
| 1.11E+05 | 20.80 |
| 3.70E+04 | 22.32 |
| 1.23E+04 | 24.23 |

Figure 9:
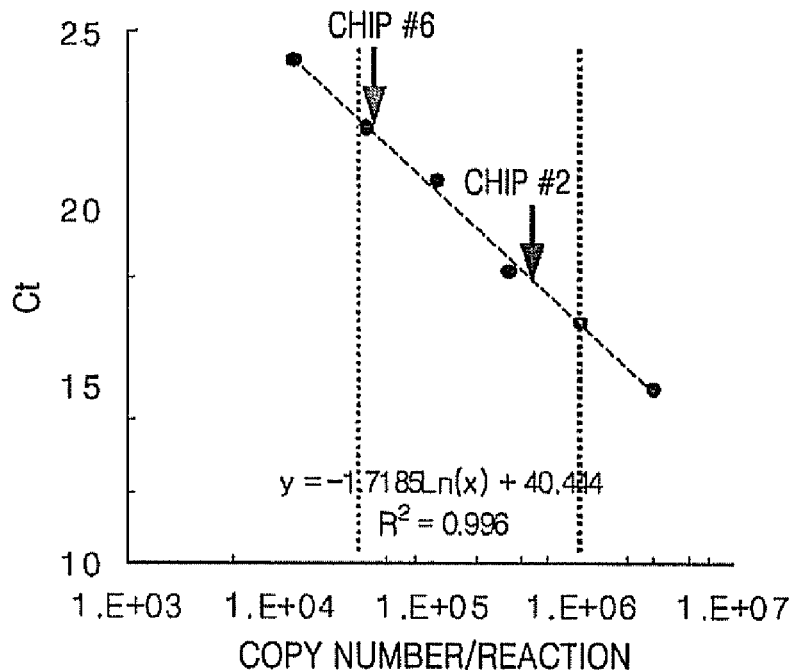
FIG. 9 is a standard curve showing exemplary Ct values according to the copy number of target genes of *E. coli* BL21 gDNA, in which the Ct values of tested chips (Chip #2 and Chip #6) after nucleic acid concentration were assigned to corresponding position on the standard curve.

Using the data shown in Table 2, a standard curve that represents Ct values according to the target gene copy number of *E. coli* BL21 gDNA was formed. FIG. 9 is a standard curve showing Ct values according to the copy number of target genes of *E. coli* BL21 gDNA, according to an embodiment. In FIG. 9, the right dotted line refers to Ct values corresponding to the point at which all of the *E. coli* BL21 gDNA is ideally concentrated up to 40 times without loss (1.00E+06 copy), and the left dotted line refers to Ct values corresponding to an original BL21 gDNA solution (16700 copy/µl) prior to concentration. As shown in FIG. 9, in the case of p number 6 which has no pillar structure, the concentration efficiency of DNA is low and therefore the Ct values are relatively high, but in the case of chip number 2, the concentration efficiency of DNA is very high and therefore Ct values are very low. A plot of chip number 2 represents Ct values corresponding to 35% of the total number of 1.00E+06 copy. Accordingly, it can be seen that a 65% loss occurred for the process with a 40 times (i.e., 40×) concentration, but a considerable amount of DNA was concentrated.

EXAMPLE 6

Concentration and Amplification Efficiency of Nucleic Acid Using Cell Lysate

Figure 10:
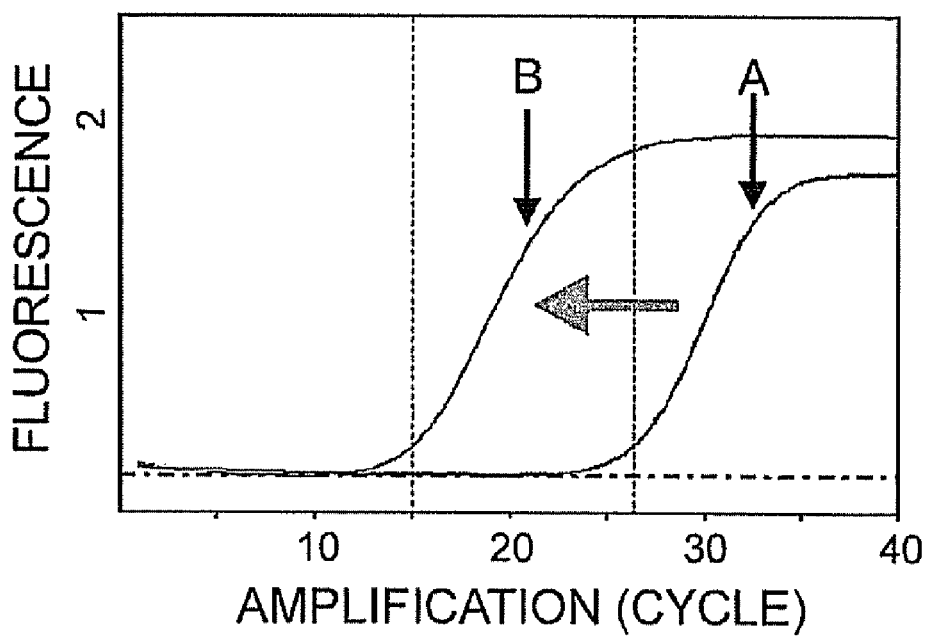
FIG. 10 is a graph showing an exemplary increase of PCR efficiency according to nucleic acid concentration and purification from cell lysate, according to an embodiment.

Concentration and amplification efficiency of nucleic acid were determined using $1.3 \times 10^5$ cell/µl of *E. coli* BL21 lysate. In DNA concentration, an aqueous mixture of sodium sulfate and sodium acetate (1 M in each salt, pH 3.0) was used as a binding buffer, and an aqueous mixture of sodium sulfate and sodium acetate (0.01 M in each salt, pH 3.0) was used as a washing buffer. PCR was performed in the same manner as in Example 4. FIG. 10 is a graph showing PCR efficiency according to nucleic acid concentration, according to an embodiment. In FIG. 10, curve A represents results of performing PCR for nucleic acid from an initial DNA solution prior to concentration, and curve B represents PCR results of DNA concentrated using the method of concentrating and amplifying nucleic acid according to an embodiment. Referring to FIG. 10, it can be seen that the Ct value prior to concentration was 25.5, but a Ct value after nucleic acid concentration was significantly decreased to 15.37. That is, when the method of concentrating and amplifying nucleic acid according to an embodiment is used, nucleic acid can be efficiently concentrated, purified and amplified even in cell lysate in which a large amount of PCR inhibitor exists.

To quantitatively determine the concentration efficiency of nucleic acid using the method of concentrating and amplifying nucleic acid according to an embodiment, Ct values using the cell number of *E. coli* BL21 as a template were measured. The results are shown in Table 3.

TABLE 3

| Cell number | Ct |
|---|---|
| 1.00E+07 | 19.69 |
| 3.33E+06 | 21.24 |
| 1.11E+06 | 22.72 |
| 3.70E+05 | 24.74 |
| 1.23E+05 | 26.37 |
| 4.12E+04 | 27.80 |

Figure 11:
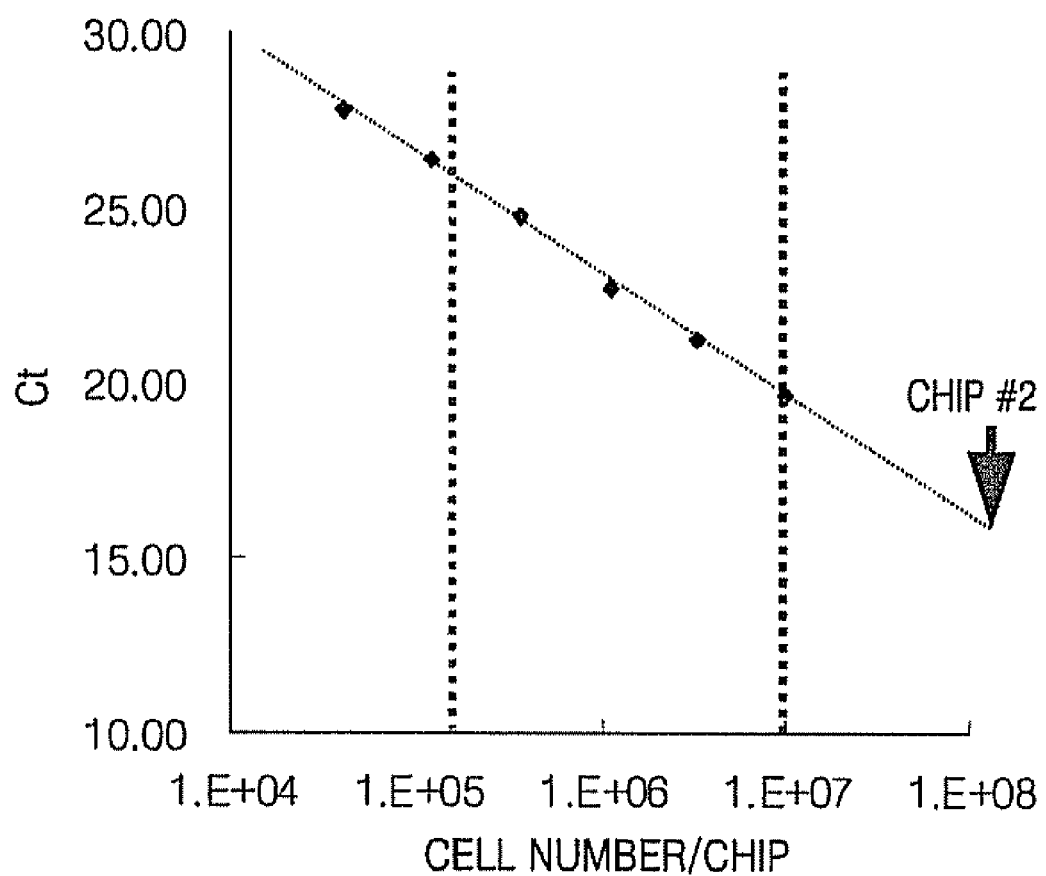
FIG. 11 is a standard curve showing exemplary Ct values according to the number of *E. coli* BL21 cells, in which the Ct value of tested chip (Chip #2) after nucleic acid concentration was assigned to corresponding position on the standard curve.

Using the data shown in Table 3, a standard curve that represents Ct values according to the cell number of *E. coli* BL21 was completed. FIG. 11 is a standard curve showing Ct values with the cell number of *E. coli* BL21, according to an embodiment. In FIG. 11, a right dotted line refers to a Ct value (19.69) corresponding to when *E. coli* BL21 cells are ideally concentrated up to 50 times ($1 \times 10^7$ cell/µl), and a left dotted line refers to a Ct value corresponding to the cell number of an original BL21 ($1.3 \times 10^5$ cell/µl) prior to concentration. Referring to FIG. 11, in the case of chip number 2, a Ct value is significantly lower than 19.69. When a Ct value corresponding to chip number 2 is converted to the cell number, it represents greater than about 500 times the concentration of the original cell. This is because PCR inhibitors present in cell lysate were removed during the process of concentrating nucleic acid and thus nucleic acid was obtained in purer form. Therefore, when the method of concentrating and amplifying nucleic acid according to an embodiment is used, cell lysate including PCR inhibitors can be efficiently purified, concentrated, and amplified.

According to the present invention, since nucleic acid is reversibly bound on the interior surface of a micro chamber, PCR recovery yield is higher compared with a surface of aluminum oxide in which irreversible binding generally occurs. In addition, all the processes are sequentially performed in a single micro chamber so that the number of samples and consumables can be reduced, time and labor consumed in treatment and analysis can be reduced, detection sensitivity can be improved due to no sample loss by removing a process of transporting a sample, and a danger of cross contamination can be significantly reduced. Therefore, the apparatus and method of the present invention can readily be used to provide a complete, automated system for concentration and amplification of nucleic acid.

While the present invention has been particularly shown and described with reference to exemplary embodiments thereof, it will be understood by those of ordinary skill in the art that various changes in form and details may be made therein without departing from the spirit and scope, as defined by the following claims.

What is claimed is:

1. A method of sequentially performing concentration and amplification of nucleic acid in a single micro chamber, the method comprising:
introducing a nucleic acid-containing sample and a solution comprising a kosmotropic salt to a micro chamber having a hydrophilic interior surface to concentrate nucleic acid by binding the nucleic acid on the interior surface of the micro chamber; and
performing a polymerase chain reaction (PCR) by adding a PCR mixture to the micro chamber,
wherein the performing PCR comprises adding polyethylene glycol and bovine serum albumin (BSA) to the micro chamber, and
wherein concentrations of the polyethylene glycol and bovine serum albumin (BSA) are 2.5-10% by volume and 0.1-10 mg/ml, respectively, and
wherein the kosmotropic salt is at least one selected from the group consisting of phosphate ($HPO_4^{2-}$), hydroxide ($OH^-$), fluoride ($F^-$), formate ($HCOO^-$), and sodium sulfate ($Na_2SO_4$).

2. The method of claim 1, wherein the concentrating the nucleic acid further comprises washing the interior surface of the micro chamber to remove any of the nucleic acid-containing sample that is not bound.

3. The method of claim 1, wherein the interior surface of the micro chamber has a plurality of pillars.

4. The method of claim 3, wherein an interval between the pillars is 8 to 50 μm.

5. The method of claim 1, wherein the hydrophilic interior surface has a hydrophilic functional group selected from the group consisting of a hydroxyl group, an amine group, a carboxyl group, a polycarboxyl group, and a silanol group.

6. The method of claim 1, wherein the kosmotropic salt further comprises acetate ($CH_3COO^-$).

7. The method of claim 1, wherein the nucleic acid-containing sample and kosmotropic salt have a pH of 3-10.

8. The method of claim 1, wherein the concentration of the kosmotropic salt is 100 to 2,000 mM.

9. The method of claim 1, wherein the nucleic acid-containing sample is blood, serum, urine, saliva, or cell lysate of bacteria existing in a cell culture fluid.

10. The method of claim 1, wherein the concentration of the polyethylene glycol is 2.5-5% by volume.

11. The method of claim 1, wherein the concentration of the bovine serum albumin (BSA) is 0.62-10 mg/ml.

12. A method of sequentially performing concentration and amplification of nucleic acid in a single micro chamber, the method comprising:
introducing a nucleic acid-containing sample and a solution comprising a kosmotropic salt comprising sodium sulfate and sodium acetate, to a micro chamber having a hydrophilic interior surface comprising silanol groups and having a plurality of pillars, wherein the pillars have a diameter of 25-50 μm and an interval between the pillars is 8 to 17 μm, to concentrate nucleic acid by binding the nucleic acid on the interior surface of the micro chamber; and
performing a polymerase chain reaction (PCR) by adding a PCR mixture to the micro chamber,
wherein the performing PCR comprises adding polyethylene glycol and bovine serum albumin (BSA) to the micro chamber, and
wherein concentrations of the polyethylene glycol and bovine serum albumin (BSA) are 2.5-10% by volume and 0.1-1.25 mg/ml, respectively.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
yccakactcc tacgggaggc                     20

<210> SEQ ID NO 2
<211> LENGTH: 22
<212> TYPE: DNA
<213> ORGANISM: Artificial Sequence
<220> FEATURE:
<223> OTHER INFORMATION: reverse primer

<400> SEQUENCE: 2
gtattaccgc rrctgctggc ac                  22